United States Patent [19]

Bacon et al.

[11] Patent Number: 5,372,800
[45] Date of Patent: Dec. 13, 1994

[54] COMPOSITIONS OF IODOPHENYL ESTERS AND IODOPHENYL SULFONATES IN FILM-FORMING MATERIALS FOR VISUALIZATION OF THE GASTROINTESTINAL TRACT

[75] Inventors: Edward R. Bacon, Rensselaer; Sol J. Daum; Kimberly G. Estep, both of Albany, all of N.Y.; Kurt A. Josef, Clifton Park, Pa.; Brent D. Douty, Coatesville, Pa.; Carl R. Illig, Phoenixville, Pa.

[73] Assignee: Sterling Winthrop Inc., Malvern, Pa.

[21] Appl. No.: 192,234

[22] Filed: Feb. 4, 1994

Related U.S. Application Data

[62] Division of Ser. No. 40,702, Mar. 31, 1993, Pat. No. 5,336,484.

[51] Int. Cl.$^5$ ............................................. A61K 49/04
[52] U.S. Cl. ............................... 424/5; 514/506; 558/51; 558/53; 558/54
[58] Field of Search ............... 424/5; 514/506; 558/51, 558/53, 54

[56] References Cited

U.S. PATENT DOCUMENTS 2,348,231  5/1944  Strain et al. ............... 260/476

(List continued on next page.)

FOREIGN PATENT DOCUMENTS

| 1259565 | 9/1989 | Canada . |
| 1481943 | 5/1967 | France . |
| 51-151514 | 10/1976 | Japan . |
| 57-140704 | 8/1982 | Japan . |
| 4807702 | 10/1993 | Japan . |

OTHER PUBLICATIONS

Yoshikawa, T. et al, Chem. Abst, 70(1):3539 pp. 318–319 (1969).

(List continued on next page.)

Primary Examiner—Gary E. Hollinden
Attorney, Agent, or Firm—Arthur Rosenstein; Imre Balogh

[57] ABSTRACT

Disclosed are x-ray contrast compositions for oral or retrograde examination of the gastrointestinal tract comprising a polymeric material capable of forming a coating on the gastrointestinal tract and an x-ray producing agent of the formula

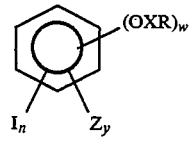

and methods for their use in diagnostic radiology of the gastrointestinal tract wherein

X=

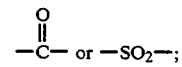

$-\overset{\overset{O}{\|}}{C}-$ or $-SO_2-$;

Z=H, halo, $C_1$–$C_{20}$ alkyl, cycloalkyl, lower alkoxy, cyano, where the alkyl and cycloalkyl groups can be substituted with halogen or halo-lower-alkyl groups;

R=$C_1$–$C_{25}$ alkyl, cycloalkyl, aryl or halo-lower-alkyl, optionally substituted with halo, fluoro-lower-alkyl, lower-alkoxy, hydroxy, carboxy or lower-alkoxy carbonyl, lower-alkenyl, lower-alkynyl, lower-alkylene or lower-alkoxy-carbonyloxy, n is 1–5;
y is 0–4; and
w is 1–4.

25 Claims, No Drawings

U.S. PATENT DOCUMENTS

| | | | |
|---|---|---|---|
| 2,622,100 | 12/1952 | Newbery et al. | 260/612 |
| 2,832,722 | 8/1958 | Singher | 167/95 |
| 3,360,436 | 12/1967 | Felder et al. | 167/95 |
| 3,361,700 | 1/1968 | Archer et al. | 260/31.4 |
| 3,574,718 | 4/1971 | Bjork et al. | 260/501.11 |
| 3,795,698 | 3/1974 | Soulal et al. | 260/471 R |
| 3,825,591 | 7/1974 | Felder et al. | 260/519 |
| 4,038,379 | 7/1977 | Elinov et al. | 424/4 |
| 4,069,306 | 1/1978 | Rothman | 424/4 |
| 4,120,946 | 10/1978 | Quemille et al. | 424/4 |
| 4,835,304 | 5/1989 | Williams | 560/144 |
| 5,019,370 | 5/1991 | Jay et al. | 424/4 |

OTHER PUBLICATIONS

Wang, et al, Yaoxne Xuebao, vol. 16, (8), pp. 610–617, Aug. 1981.

James et al, Pharm, Acta Helvetiae, 47, 244–256 (1972).

Hashimoto et al (Japanese Kokai Pat. Appln. No. Sho 55-127322 (1980).

Wentworth, S. E. et al., *Organic Preparation and Procedures,* 1(4):225–228 (1969).

Schmidt, B., et al. *Chem. Ber.* 125(6):1501–1506, (1992).

Motherwell, W. B. et al. *J. Chem. Soc. Chem. Commun.* (13):877–879 (1991).

Fu, J. M. et al. *Tetrahedron Letters,* 31(12):1665–1668 (1990).

Matsumoto, T. et al., *Tetrahedron Letters,* 32(46):6735–6736 (1991).

Echavarren, A. M. et al. *J. American Chemical Society,* 109(18):5478–5486 (1987).

Matsumoto, T. et al., *Synlett* (11):843–846 (1993).

COMPOSITIONS OF IODOPHENYL ESTERS AND IODOPHENYL SULFONATES IN FILM-FORMING MATERIALS FOR VISUALIZATION OF THE GASTROINTESTINAL TRACT

This application is a division of application Ser. No. 08/040,702, filed Mar. 31, 1993 now U.S. Pat. No. 5,336,484.

BACKGROUND OF THE INVENTION

1. Field of the Invention

This invention relates to x-ray contrast compositions containing the contrast agents iodophenyl esters and iodophenyl sulfonates, and methods for their use in diagnostic radiology of the gastrointestinal tract.

2. Reported Developments

Roentgenographic examination utilizing x-rays and computed tomography (hereinafter CT) scans of fractures and other conditions associated with the skeletal system is routinely practiced without the use of contrast agents. X-ray visualization of organs containing soft tissue, such as the gastrointestinal (hereinafter GI) tract, requires the use of contrast agents which attenuate X-ray radiation. D. P. Swanson et al in "Pharmaceuticals In Medical Imaging", 1990, MacMillan Publishing Company, provides an excellent background in medical imaging utilizing contrast agents and compositions therewith.

Roentgenographic examination of the GI tract are indicated for conditions of digestive disorders, changes in bowel habit, abdominal pain, GI bleeding and the like. Prior to radiological examination, administration of a radiopaque contrast medium is necessary to permit adequate delineation of the respective lumen or mucosal surface from surrounding soft tissues. Accordingly, a contrast medium is administered orally to visualize the mouth, pharynx, esophagus, stomach, duodenum and proximal small intestine. The contrast medium is administered rectally for examination of the distal small intestine and the colon.

The most widely used contrast agent for the visualization of the GI tract is barium sulfate administered as a suspension orally or rectally as an enema. (See, for example, U.S. Pat. Nos.: 2,659,690; 2,680,089; 3,216,900; 3,235,462; 4,038,379 and 4,120,946) Notwithstanding its relatively good contrast characteristics, negligible absorption from the GI tract following oral or rectal administration and speedy excretion from the body, barium sulfate has certain disadvantages. In the presence of intestinal fluids it lacks homogeneity and poorly adheres to mucus membranes which can result in poor X-ray images. In the colon, when administered as an enema, it flocculates and forms irregular clumps with fecal matter.

Iodinated organic compounds have also been used as GI contrast agents since the iodine atom is an effective x-ray absorber. They have the most versatility and are utilized in the widest variety of procedures. They are very absorptive of x-rays with which the iodine interacts and produce a so-called photoelectric effect which is a large magnification in contrast caused by the photons stopped in the iodine-containing medium. The magnification of contrast exceeds the level that would be expected from relative changes in density. Because of this magnification, relatively low concentrations of the contrast agent can be utilized. (For iodinated agents see, for example, U.S. Pat. Nos.: 2,786,055; 3,795,698; 2,820,814; 3,360,436; 3,574,718, 3,733,397; 4,735,795 and 5,047,228.)

The desiderata for an ideal GI contrast agent includes: good toxicological profile; the ability to fill the entire bowel/lumen and evenly coat the gut mucosa so that the presence of the bowel is detectable when the lumen is not distended; and nonirritation to the intestinal mucosa; and passage through the GI tract without producing artifacts or stimulating vigorous intestinal peristalsis.

These requirements were addressed by many investigators and their efforts resulted in great improvements over the years. The requirement of evenly coating the gut mucosa with a contrast agent to effectively cover the walls of the intestines proved to be rather difficult. Without meeting these requirements it is impossible to obtain X-ray pictures of high precision. To that end, the use of certain polymer additives were proposed as illustrated hereunder.

U.S. Pat. No. 4,069,306 discloses an x-ray contrast preparation which is said to adhere to the walls of body cavities. The preparation comprises a finely divided water-insoluble inorganic x-ray contrast agent and minute particles of a hydrophilic polymer which is insoluble in water but is water-swellable. The body cavity is supplied with such preparation suspended in water. The x-ray contrast agent is present in admixture with and/or enclosed in and/or adhered to said minute polymer particles.

U.S. Pat. No. 4,120,946 discloses a pharmaceutical composition for barium opacification of the digestive tract, comprising colloidal barium sulfate and a polyacrylamide in an aqueous vehicle. The polyacrylamide forms a viscous solution at low concentration which makes it possible to maintain the barium sulfate in suspension and at the same time permit good adherence of the preparation to the walls of the organ which it is desired to x-ray.

U.S. Pat. No. 5,019,370 discloses a biodegradable radiographic contrast medium comprising biodegradable polymeric spheres which carry a radiographically opaque element, such as iodine, bromine, samarium and erbium. The contrast medium is provided either in a dry or liquid state and may be administered intravenously, orally and intra-arterially.

While these polymeric materials greatly enhance attachment of the contrast agent used therewith to the walls of organs for better visualization thereof, they do not provide a uniform coating thereon. As such, there is still a need for an improved x-ray imaging medium that uniformly coats the soft tissues subjected to diagnostic x-ray examination.

SUMMARY OF THE INVENTION

It is the object of the present invention to provide compositions for coating the gastrointestinal tract of mammals to form an effective radiopaque coating thereon by which diagnostic examination of the GI tract may be accomplished. To that end, a thin coating is formed on the inner surface of the GI tract effected by ingesting, prior to visualization by an X-ray emitting device, a polymeric film former, which has incorporated therein an X-ray contrast agent, capable of coating the GI tract. The removal of the coating occurs as a result of the normal turnover of cells, that is, within about 24 to 48 hours. Such compositions must meet several requirements: both the X-ray contrast agent and the film former must be nontoxic; must not contain leachable or digestible components that would deleteriously affect the patient; and the composition must be capable of forming a film in the pH range of from about 5 to about 8.

The object of the present invention is achieved by a composition comprising: an X-ray contrast agent; a polymeric material which is at least partially water soluble and contains polarizable or ionizable groups; and a divalent metal ion selected from the group consisting of $Mg^{++}$, $Ca^{++}$, $Zn^{++}$ and $Ba^{++}$ which potentiates the effect of the polymeric material as a film former on the mucosa of the GI tract.

The contrast agent, polymeric film former and the divalent metal ion are incorporated in a solid or liquid media for administration to a mammal for X-ray visualization of the GI tract.

In accordance with the invention there is further provided a method for x-ray diagnostic imaging of the GI tract which comprises orally or rectally administering to the patient an effective contrast producing amount of one of the above-described x-ray contrast compostions.

The composition for radiological examination of the GI tract comprises a compound of the formula:

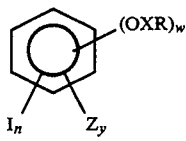

wherein
X=

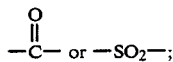

Z=H, halo, $C_1$-$C_{20}$ alkyl, cycloalkyl, lower alkoxy, cyano, where the alkyl and cycloalkyl groups can be substituted with halogen or halo-lower-alkyl groups;

R=$C_1$-$C_{25}$ alkyl, cycloalkyl, aryl or halo-lower-alkyl, optionally substituted with halo, fluoro-lower-alkyl, lower-alkoxy, hydroxy, carboxy or lower-alkoxy carbonyl, lower-alkenyl, lower-alkynyl, lower-alkylene or lower-alkoxy-carbonyloxy, n is 1–5;
y is 0–4; and
w is 1–4.

As used herein, the term halogen (or halo) means fluorine, chlorine, bromine or iodine.

As used herein, the term cycloalkyl means carbocyclic rings having from three to eight ring carbon atoms including cyclopropyl, cyclobutyl, cyclopentyl, cyclohexyl and cyclooctyl which may be substituted on any ring carbon atom thereof by one or more lower-alkyl groups, lower-alkoxy groups or halogens.

As used herein the terms lower-alkyl and lower-alkoxy mean monovalent aliphatic radicals, including branched chain radicals, of from one to ton carbon atoms. Thus, the lower-alkyl moiety of such groups include, for example, methyl, ethyl, propyl, isopropyl, n-butyl, sec-butyl, t-butyl, n-pentyl, 2-methyl-3-butyl, 1-methylbutyl, 2-methylbutyl, neopentyl, n-hexyl, 1-methylpentyl, 3-methylpentyl, 1-ethylbutyl, 2-ethylbutyl, 2-hexyl, 3-hexyl, 1,1,3,3-tetramethylpentyl, 1,1-dimethyloctyl and the like.

As used herein, the term lower-alkenyl and lower-alkynyl means monovalent, unsaturated radicals including branched chain radicals of from three to ten carbon atoms and thus include 1-ethenyl, 1-(2-propenyl), 1-(2-butenyl), 1-(1-methyl-2-propenyl), 1-(4-methyl-2-pentenyl), 4,4,6-trimethyl-2-heptenyl, 1-ethynyl, 1-(2-propynyl), 1-(2-butynyl), 1-(1-methyl-2-propynyl), 1-(4-methyl-2-pentynyl) and the like.

As used herein, the term alkylene means divalent saturated radicals, including branched chain radicals of from two to ten carbon atoms having their free valences on different carbon atoms and thus includes 1,2-ethylene, 1,3-propylene, 1,4-butylene, 1-methyl-1, 2-ethylene, 1,8-octylene and the like.

As used herein, the term aryl means an aromatic hydrocarbon radical having six to ten carbon atoms. The preferred aryl groups are phenyl, substituted phenyl and naphthyl substituted by from one to three, the same or different members of the group consisting of lower-alkyl, halogen, hydroxy-lower-alkyl, alkoxy-lower-alkyl and hydroxy.

The x-ray contrast compound can comprise one, two, three or more iodine atoms per molecule; preferred species contain at least two, and more preferably, at least three iodine atoms per molecule.

The solid x-ray contrast agents in particulate forms useful in the practice of the present invention can be prepared by techniques known in the art. The solid agents are comminuted to the desired size using conventional milling methods, such as airjet or fragmentation milling. We have found that an effective average particle size of less than about 100 μ provides for good distribution and coating in the GI tract. As used herein, particle size refers to a number average particle size as measured by conventional techniques, such as sedimentation field flow fractionation and disk centrifugation. An effective average particle size of less than about 100 μ means that at least about 90% of the particles have a weight average particle size of less than about 100 μ as measured by art recognized techniques.

The polymers that were found to be suitable for forming a thin coating on the GI tract can be classified as anionic, cationic and neutral polymers, a description of which follows. U.S. Pat. No. 4,623,539, the disclosure of which is incorporated by reference, pertains to such polymers.

The contrast agent is incorporated in the polymeric material along with the divalent cation by any suitable techniques, such as by mixing, blending, precipitating or by enclosing the contrast agent into minute polymeric particles.

The contrast agent, polymeric material and divalent cation blend is then formulated for administration using physiologically acceptable carriers or excipients in a manner within the skill of the art. The contrast agent with the addition of pharmaceutically acceptable aids (such as surfactants and emulsifiers) and excipients may be suspended or partially dissolved in an aqueous medium resulting in a dispersion, solution, suspension or emulsion. Alternatively, the contrast agent, polymeric material and divalent cation may be formulated into a solid form, such as tablets or capsules.

A method for diagnostic imaging of the GI tract for use in medical procedures in accordance with this invention comprises orally or rectally administering to the mammalian patient in need of x-ray examination, an effective contrast producing amount of a composition of the present invention. After administration, at least a portion of the GI tract containing the administered composition is exposed to x-rays to produce an x-ray image pattern corresponding to the presence of the contrast agent, then the x-ray image is visualized and interpreted using techniques known in the art.

DETAILED DESCRIPTION OF THE INVENTION

Compounds of the present invention can be made according to the schematic procedure shown or other methods using commercially available starting materials, intermediates and reagents. Starting materials, reagents and solvents can be obtained from chemical suppliers such as Aldrich, Baker and Eastman Chemical Companies, or they may be prepared by techniques known in the art.

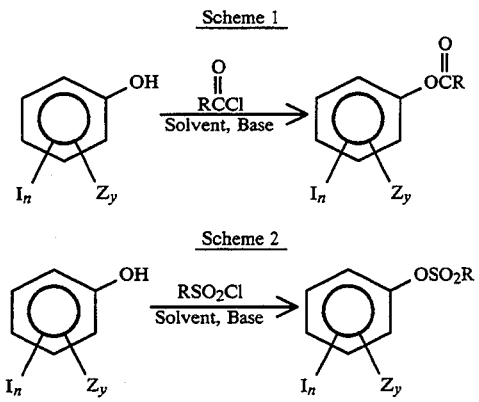

wherein Z, R, n and y are as previously described.

The following examples will further illustrate the compounds used in the present invention.

EXAMPLE 1

2,4,6-Triiodophenyl 2-ethylhexanoate

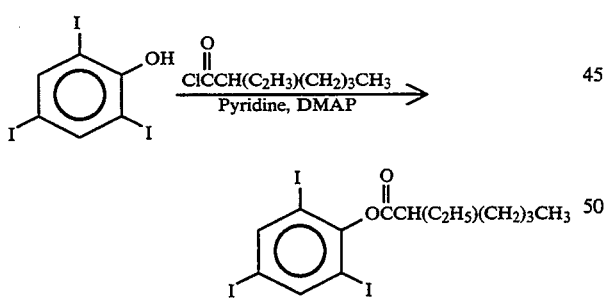

A solution of 2,4,6-triiodophenol (20.0 g, 42 mmol), 2-ethylhexanoyl chloride (25 ml, 144 mmol, 3.5 eq.) and 4-dimethylaminopyridine (DMAP; 2 mmol, 250 mg, 0.05 eq.) in 150 ml of pyridine was stirred overnite at room temperature. The solution was poured into 1000 ml of 1 N aqueous hydrochloric acid and the aqueous solution was extracted twice with ethyl acetate. The combined organic layers were washed with aqueous hydrochloric acid, water, saturated aqueous sodium chloride and then dried over magnesium sulfate. The ethyl acetate solution was then concentrated under vacuum to give an oil (30 g) which was purified by silica gel chromatography (5% ethyl acetate/hexanes eluent) to give the product. Concentration under high vacuum afforded 21 g (79%) of the desired hexanoate ester as an oil. The product was taken up in hexanes and filtered through a pad of basic alumina. The filtrate was concentrated under high vacuum to give 16.9 g of analytically pure product.

Title Compound: $^1$H (300 MHz) and $^{13}$C (75 MHz) NMR spectra were consistent with the desired structure. Calculated for $C_{14}H_{17}I_3O_2$: C, 28.12; H, 2.87; I, 63.66. Found: C, 28.27; H, 2.79; I, 63.62.

EXAMPLE 2

2,4,6-Triiodophenyl 2-methylpentanoate

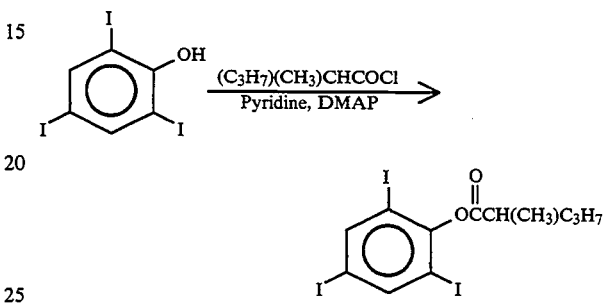

Using the procedure described for the synthesis of 2,4,6-triiodophenyl (2-ethyl)hexanoate, 2,4,6-triiodophenyl 2-methylpentanoate was prepared in 25% yield as a solid, mp. 66°–68° C., from 2,4,6-triiodophenol (15.0 g, 31.8 mmol), 2-methylvaleryl chloride (4.6 g, 34.2 mmol, 1.07 eq.) and a catalytic amount (0.1 g) of 4-dimethylaminopyridine in dry pyridine (20 ml).

Title Compound: $^1$H (300 MHz) and $^{13}$C (75 MHz) NMR spectra were consistent with the desired structure. Calculated for $C_{12}H_{13}I_3O_2$: C, 25.29; H, 2.30; I, 66.80. Found: C, 25.36; H, 2.13; I, 66.57.

EXAMPLE 3

2,4,6-Triiodophenyl 3-cyclopentyl propionate

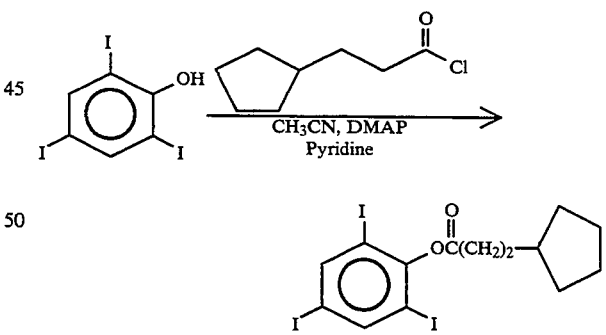

A solution of 2,4,6-triiodophenol (15.0 g, 31.8 mmol), 3-cyclopentylpropionyl chloride (14.6 ml, 95.4 mmol, 3 eq), pyridine (2.83 ml, 35.0 mmol, 1.1 eq) and 4-dimethylaminopyridine (200 mg) in 150 ml of acetonitrile was heated to reflux under argon for 21 hrs and then cooled. The reaction solution was washed with water, saturated aqueous sodium chloride and then dried over magnesium sulfate. The organic layer was filtered and concentrated under vacuum. The resulting residue was purified by silica gel chromatography (1% ethyl acetate/hexanes) to give 19.17 g of solid product. The solid was recrystallized from hexanes to give the final product as a feathery white solid.

Title Compound: $^1$H (300 MHz) and $^{13}$C (75 MHz) NMR spectra were consistent with the desired structure. Calculated for $C_{14}H_{15}I_3O_2$: C, 28.21; H, 2.54; I, 63.88. Found: C, 28.25; H, 2.44; I, 64.06.

EXAMPLE 4

2,4,6-Triiodophenyl (2-propyl)pentanoate

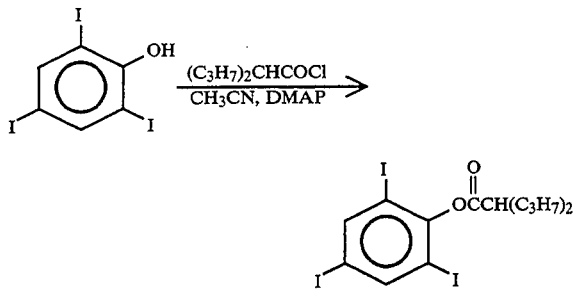

A mixture of 2,4,6-triiodophenol (2.0 g, 4.24 mmol), 2-propylvaleroyl chloride (2.5 ml, 12.7 mmol, 3 eq) and 4-dimethylaminopyridine (DMAP; 20 mg) in 20 ml of acetonitrile was refluxed under argon overnite. The reaction mixture was cooled and poured into excess aqueous sodium bicarbonate and then extracted with dichloromethane. The dichloromethane extract was dried over magnesium sulfate, filtered, and evaporated to give the crude product (2.42 mmol, 95%) as a pink solid. Recrystallization from ethyl acetate gave 1.75 g (68%) of pure product, mp 99°–101° C.

Title Compound: $^1$H (300 MHz) and $^{13}$C (75 MHz) NMR spectra were consistent with the desired structure. Calculated for $C_{14}H_{17}I_3O_2$: C, 28.12; H, 2.87; I, 63.66. Found: C, 28.35; H, 2.80; I, 63.74.

EXAMPLE 5

2,4,6-Triiodophenol perfluoroheptanoate

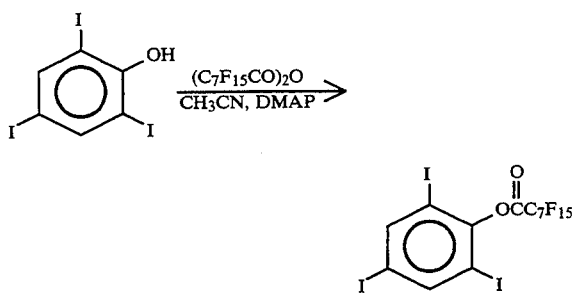

A mixture of 2,4,6-triiodophenol (2.0 g, 4.24 mmol), perfluoroheptanoic anhydride (10.3 g, 12.7 mmol, 3 eq) and 4-dimethylaminopyridine (DMAP; 20 mg) in 20 ml of acetonitrile was heated to reflux under argon for 5 hrs. on cooling, the resulting solution separated into two layers whereupon the lower layer solidified. The solids were collected and the filtrate was poured into excess saturated aqueous sodium bicarbonate. The aqueous mixture was extracted with dichloromethane; the organic layer was dried over magnesium sulfate, filtered and concentrated in vacuo to give an off-white solid. The solid was recrystallized from methanol to give the desired product (0.51 g, 14%) as white needles, mp 71°–73° C.

Title Compound: $^1$H (300 MHz) and $^{13}$C (75 MHz) NMR spectra were consistent with the desired structure. Calculated for $C_{14}H_2F_{15}I_3O_2$: C, 19.38; H, 0.23; I, 43.87. Found: C, 19.16; H, 0.02; I, 43.78.

EXAMPLE 6

2,4,6-Triiodophenyl-tris-(2-cyclohexanoate)

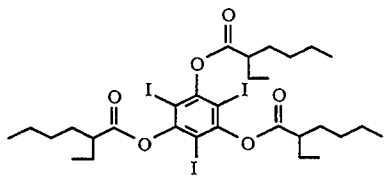

The method of F. L. Weitle, J. Org. Chem. 41, 2044–2045 (1976) was used to prepare 2,4,6-triiodophloroglucinol.

A mixture of 10.00 g (19.8 mmol) of 2,4,6-triiodophloroglucinol, 17.1 g (118.8 mmol) of 2-ethylhexanoic acid, 149.7 g (712.8 mmol) of trifluoroacetic anhydride and 50 ml of anhydrous toluene was refluxed for 18 hrs. The dark red solution was concentrated in vacuo to produce a brown oil. The oil was partitioned between 250 ml of ethyl acetate and 100 ml of 5% potassium carbonate solution and the ethyl acetate layer was washed with saturated sodium bicarbonate solution (100 ml), brine (50 ml) and dried over sodium sulfate. Concentration in vacuo produced a brown oil. The oil was purified by flash chromatography on 713 g of silica gel with 5% ethyl acetate/hexane as the eluent. Concentration in vacuo produced 16.25 g (93%) of product as a yellow oil.

Title Compound: $^1$H (300 MHz) and $^{13}$C (75 MHz) NMR spectra were consistent with the desired structure. FAB/MS: $(M+1)^+ 883$.

EXAMPLE 7

2,4,6-Triiodophenyl dodecanoate

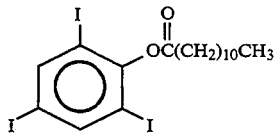

Dodecanoyl chloride (2.95 ml, 12.8 mmol) was added to a suspension of 2,4,6-triiodophenol (6.0 g, 12.7 mmol) in refluxing acetonitrile (50 ml) and the mixture was heated under argon for 24 hrs. The reaction mixture was cooled and washed with saturated aqueous sodium bicarbonate. The organic layer was dried over magnesium sulfate, filtered, and evaporated to dryness under vacuum to give an off-white solid. The crude product was recrystallized from methanol to give 6.9 g (83%) of the desired ester, mp 68°–69° C.

Title Compound: $^1$H (300 MHz) and $^{13}$C (75 MHz) NMR spectra were consistent with the desired structure. Calculated for $C_{18}H_{25}I_3O_2$: C, 33.05; H, 3.85; I, 58.20. Found: C, 32.91; H, 3.75; I, 58.25.

EXAMPLE 8

3-Trifluoromethyl-2,4,6-triiodophenyl 2-ethyl hexanoate

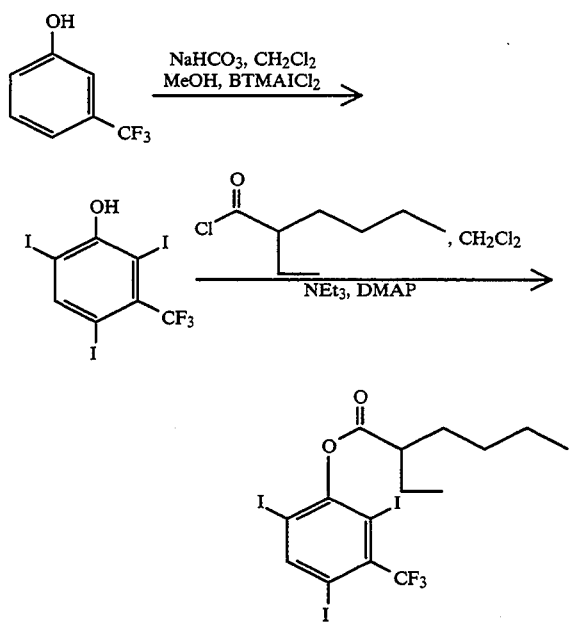

A mixture of 9.00 g (55.5 mmol) of α,α,α,-trifluoro-m-cresol, 31.4 g (374 mmol) of NaHCO$_3$ and 59.9 g (172 mmol) of benzyltrimethytammonium dichloroiodate in 78 ml dichloromethane/30 ml methanol was placed under nitrogen and stirred for 22 hrs. The mixture was filtered and the NaHCO$_3$ was washed with 200 ml of dichloromethane. The filtrate was washed with 1M HCl (150 ml) 5% NaHSO$_3$ (100 ml) and brine (100 ml). The solution was dried over Na$_2$SO$_4$ and concentrated in vacuo to 27.1 g of brown solid. The solid was dissolved in a minimum amount of dichloromethane and was purified by flash chromatography on 678 g of silica gel with 30% dichloromethane/hexane as the eluent to afford 13.55 g (45%) of 3-trifluoromethyl-2,4,6-triiodophenyl 2-ethyl hexanoate as a pink solid. $^1$H-NMR (300 MHz) spectral data were consistent with the desired structure.

A mixture of 10.0 g (18.53 mmol) of 2,4,6-triiodo-3-trifluoromethyl phenol, 3.62 g (22.2 mmol) of 2-ethyl-hexanoyl chloride and 0.226 g (1.85 mmol) of 4-dimethylaminopyridine in 37 ml of dry dichloromethane was placed under nitrogen and cooled to 0° C. Triethylamine (2.25 g, 22.2 mmol) was added dropwise and the resulting solution was stirred for 16 hrs at room temperature. The mixture was partitioned between 200 ml of dichloromethane and 100 ml of 1M HCl. The dichloromethane layer was washed with saturated NaHCO$_3$ solution (50 ml) and brine (100 ml). The solution was dried over Na$_2$SO$_4$ and concentrated in vacuo to 12.80 g of brown oil. The oil was purified by flash chromatography on 20 g of silica gel with 3% ethyl acetate/hexane as the eluent. Concentration in vacuo afforded 11.63 g (94%) of product as a light yellow oil.

Title Compound: $^1$H (300 MHz) and $^{13}$C (75 MHz) NMR spectra were consistent with the desired structure. FAB/MS: M$^+$666. Calculated for C$_{15}$H$_{16}$F$_3$I$_3$O$_2$: C, 27.05; H, 2.42; I 57.16. Found: C, 27.47; H, 2.42; I, 56.88.

EXAMPLE 9

2,4,6-triiodophenly-bis-(2-methylpentanoate)

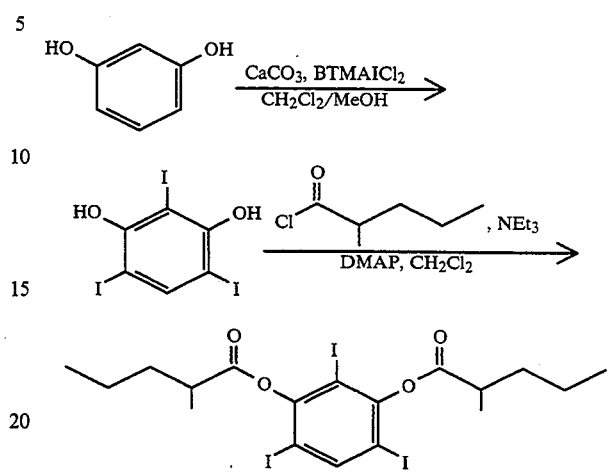

A mixture of 1.00 g (9.08 mmol) of resorcinol, 6.12 g (61.1 mmol) of calcium carbonate and 9.80 g (28.2 mmol) of benzyltrimethylammonium dichloroiodate (BTMAICl$_2$) in 13 ml dichloromethane/5 ml methanol was placed under nitrogen and stirred for 4 hrs. The mixture was filtered and concentrated in vacuo. The resulting residue was partitioned between 100 ml of ethyl acetate and 50 ml of saturated NaHCO$_3$ solution. The ethyl acetate layer was washed with brine (25 ml) and dried over Na$_2$SO$_4$. Concentration in vacuo produced a dark brown solid. The solid was dissolved in a minimum amount of ethyl acetate and was purified by flash chromatography on 100 g of silica gel with 20% ethyl acetate/hexane as the eluent. The first 125 ml to elute contained nothing while the pure product eluted with the next 224 ml. Concentration in vacuo afforded 2.78 g (63%) of 2,4,6-triiodoresorcinol as a cream colored solid. $^1$H-NMR (300 MHz) spectral data were consistent with the desired structure.

A mixture of 0.500 g (1.03 mmol) of 2,4,6-triiodoresorcinol and 0.304 g (2.26 mmol) of 2-methylpentanoyl chloride in 2 ml of dry dichloromethane was placed under nitrogen. A solution containing 0.207 g (2.05 mmol) of triethylamine and 0.125 g (1.03 mmol) dimethylaminopyridine in 2 ml of dry dichloromethane was added dropwise while stirring. After complete addition the resulting light brown solution was stirred 30 min under nitrogen. The solution was partitioned between 50 ml of dichloromethane and 50 ml of 1M HCl. The dichloromethane layer was washed with saturated NaHCO$_3$ solution (50 ml) and brine (25 ml). The solution was dried over Na$_2$SO$_4$ and concentrated in vacuo to 0.677 g of brown oil. The oil was purified by flash chromatography on 20 g of silica gel with 5% ethyl acetate/hexane as the eluent. Concentration in vacuo afforded 0.622 g (88%) of product as a colorless oil which slowly solidified over seven days.

Title Compound: $^1$H (300 MHz) and $^{13}$C (75 MHz) NMR spectra were consistent with the desired structure. FAB/MS: (M+1)$^+$685. Calculated for C$_{18}$H$_{23}$I$_3$O$_4$: C, 31.60; H, 3.39. Found: C, 31.79; H, 3.32, mp 44.5°–47.0° C.

EXAMPLE 10

2,4,6-Triiodophenyl hexanesulfonate

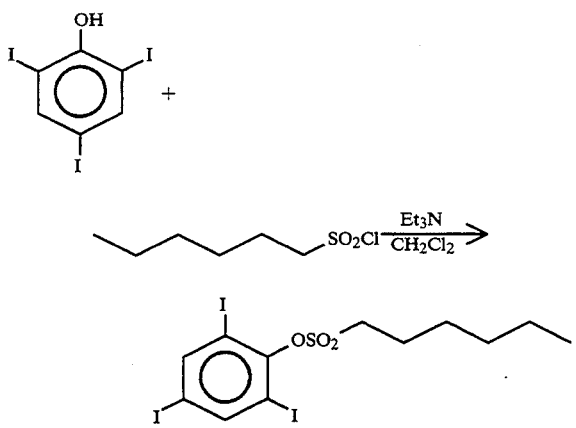

A solution of 10 g (0.021 mol) of 2,4,6-triiodophenol in 250 ml of methylene dichloride was stirred in an ice bath with 12.6 ml of triethylamine. To this solution was added dropwise 8.5 g (0.046 mol) of hexanesulfonyl chloride in 50 ml of methylene chloride. The reaction mixture was then stirred for 18 hrs at room temperature. Water was added and after separation, the organic layer was washed with saturated potassium carbonate and brine. The solution was dried over $MgSO_4$, filtered and concentrated to afford 13.5 g of crude product. Chromatography on 250 g of silica gel using 10% ethyl acetate/hexane afforded 9.8 g of product which upon recrystallization twice from hexane gave 6.5 g (50%) of 2,4,6-triiodophenyl hexanesulfonate, mp 70°–71° C.

Title Compound: $^1H$ (300 MHz) and $^{13}C$ (75 MHz) NMR spectra were consistent with the desired structure. MS; MH+621, M+620. Calculated for $C_{12}H_{15}O_3SI_3$: C, 23.47; H, 2.44; S, 5.17; I, 61.40. Found: C, 23.26; H, 2.31; S, 5.21; I, 61.32.

EXAMPLE 11

2,4,6-Triiodophenyl heptanesulfonate

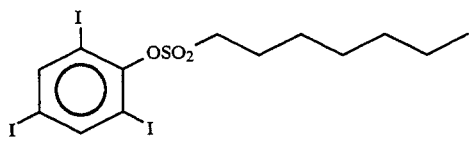

Using the same procedure as for 2,4,6-triiodophenyl hexanesulfonate, 2,4,6-triiodophenyl heptanesulfonate was prepared from 15 g (0.032 mol) of 2,4,6triiodophenol in 33% yield, mp 78°–80° C.

Title Compound: $^1H$ (300 MHz) and $^{13}C$ (75 MHz) NMR spectra were consistent with the desired structure. MS; MH+635. Calculated for $C_{13}H_{17}O_3SI_3$: C, 24.63; H, 2.70; S, 5.06; I, 60.04. Found: C, 24.71; H, 2.59; S, 5.06; I, 59.96.

EXAMPLE 12

2,4,6-Triiodophenyl decanesulfonate

Using the same procedure as for 2,4,6-triiodophenyl hexanesulfonate without the chromatography step, 2,4,6-triiodophenyl decanesulfonate was prepared from 10 g (0.021 mol) of 2,4,6-triiodophenol in 59% yield, mp 71°–72° C.

Title Compound: $^1H$ (300 MHz) and $^{13}C$ (75 MHz) NMR spectra were consistent with the desired structure. MS; MH+677. Calculated for $C_{16}H_{23}O_3SI_3$: C, 28.42; H, 3.43; I, 4.71; S, 56.31. Found: C, 28.47; H, 3.28; I, 4.73; S, 56.53.

Compositions of the Present Invention

The contrast agents may be formulated for administration using physiologically acceptable carriers or excipients in a manner within the skill of the art. The compounds with the addition of pharmaceutically acceptable aids (such as surfactants and emulsifiers) and excipients may be suspended or partially dissolved in an aqueous medium resulting in a dispersion, solution or suspension. However, the oily contrast agents are preferably made into emulsions.

Compositions of the present invention comprise the following pharmaceutically acceptable components based on % w/v:

| | |
|---|---|
| Non-aqueous phase | 1–50 |
| Polymeric Material | 0.001–15 |
| Divalent Cation | 0.001–15 |
| Contrast Agent | 0.001–75 |
| Excipient | 0–20 |
| Aids/Surfactants/Emulsifiers | 0.01–15 |
| Water | qs. to 100 |

Specific Examples of the compositions of the present invention are shown in Examples 13–15.

EXAMPLE 13

| | |
|---|---|
| 2,4,6-Triiodophenyl 2-ethylhexanoate | 23.7% (w/v) |
| Safflower Oil | 20.0% (w/v) |
| Kappa Carrageenan | 2.0% (w/v) |
| Calcium Lactate | 2.0% (w/v) |
| Tween 21 | 2.5% (w/v) |
| Hydroxypropylmethylcellulose (4000 cPs) | 0.5% (w/v) |
| q.s. with water to 100% volume and shake | |

EXAMPLE 14

| | |
|---|---|
| 2,4,6-Triiodophenyl 2-methylpentanoate | 55.3% (w/v) |
| Dow Corning Medical Antifoam AF | 40.0% (w/v) |
| Pectin | 4.0% (w/v) |
| Calcium Lactate | 2.0% (w/v) |
| q.s. with water to 100% volume and shake | |

EXAMPLE 15

| | |
|---|---|
| 12,4,6-Triiodophenyl 3-cyclopentylpropionate | 25.9% (w/v) |

-continued

| | |
|---|---|
| Simplesse ® Dietary Fat Substitute | 30.0% (w/v) |
| Heparin | 1.0% (w/v) |
| Magnesium Carbonate | 1.0% (w/v) |
| Hydroxypropylmethylcellulose (4000 cPs) | 0.5% (w/v) |
| q.s. with water to 100% volume and shake | |

The nonaqueous phase comprises vegetable oils such as safflower oil; nonmetabolizing fat substituents, such as Simplesse; fluorinated hydrocarbons, such as perfluorodecalin; mineral oil and simethicone.

Excipients advantageously used in the formulations include viscosity mediating and stabilizing agents, such as microcrystalline cellulose, ethylcellulose, hydroxypropyl methylcellulose and gum arabic. Physiologically acceptable substances may also be included, such as sodium citrate, sodium chloride, therapeutic substances, antacid substances and flavoring agents. The inclusion of antimicrobial/antiseptic agents such as methyl parahydroxybenzoate, ethyl parahydroxybenzoate, propyl parahydroxybenzoate, benzoic acid or sorbic acid may also be desirable in some formulations.

As known by those skilled in the art, surfactants or emulsifiers can reduce the interfacial tension between two immiscible phases, i.e., oil-in-aqueous medium. These agents can be used alone or in combination with other emulsifying agents and surfactants. For example, Dow Corning Medical Antifoam AF, which is a composition of 30% w/v polydimethylsiloxane simethicone and silica aerogel, 14% w/v stearate emulsifiers and 0.075% w/v sorbic acid, the balance being water, may be used by itself. Intralipid, which is an emulsion of fatty acids needs the presence of a suspending agent for it to form an acceptable emulsion with contrast agents of the present invention. The mount of such surfactants may be in the range of from 0.01 to 15% w/v of the aqueous formulations, although the amount, in general, is kept as low as possible, preferably in the range of 0.05 to 5% w/v. The surface active agents may be cationic, anionic, nonionic, zwitterionic or a mixture of two or more of these agents.

Suitable cationic surfactants include cetyl trimethyl ammonium bromide. Suitable anionic agents include sodium lauryl sulphate, sodium heptadecyl sulphate, alkyl benzenesulphonic acids and salts thereof, sodium butylnapthalene sulfonate, and sulphosuccinates. Zwitterionic surface active agents are substances that when dissolved in water they behave as diprotic acids and, as they ionize, they behave both as a weak base and a weak acid. Since the two charges on the molecule balance each other out the molecules act as neutral molecules. The pH at which the zwitterion concentration is maximum is known as the isoelectric point. Compounds, such as certain amino acids having an isoelectric point at the desired pH of the formulations of the present invention are useful in practicing the present invention.

In preparing the formulations of the present invention we prefer to use nonionic emulsifiers or surface active agents which, similarly to the nonionic contrast agents, possess a superior toxicological profile to that of anionic, cationic or zwitterionic agents. In the nonionic emulsifying agents the proportions of hydrophilic and hydrophobic groups are about evenly balanced. They differ from anionic and cationic surfactants by the absence of charge on the molecule and, for that reason, are generally less of an irritant than the cationic or anionic surfactants. Nonionic surfactants include carboxylic esters, carboxylic amides, ethoxylated alkylphenols and ethoxylated aliphatic alcohols.

One particular type of carboxylic ester nonionic surface active agents are the partial, for example mono-, esters formed by the reaction of fatty and resin adds, for example of about 8 to about 18 carbon atoms, with polyhydric alcohols, for example glycerol, glycols such as mono-, di-, tetra- and hexaethylene glycol, sorbitan, and the like; and similar compounds formed by the direct addition of varying molar ratios of ethylene oxide to the hydroxy group of fatty acids.

Another type of carboxylic esters is the condensation products of fatty and resin partial acids, for example mono-, esters ethylene oxide, such as fatty or resin acid esters of polyoxyethylene sorbitan and sorbitol, for example polyoxyethylene sorbitan, monotall oil esters. These may contain, for example, from about 3 to about 80 oxyethylene units per molecule and fatty or resin acid groups of from about 8 to about 18 carbon atoms. Examples of naturally occurring fatty acid mixtures which may be used are those from coconut oil and tallow while examples of single fatty acids are dodecanoic acid and oleic acid.

Carboxylic amide nonionic surface active agents are the ammonia, monoethylamins and diethylamine amides of fatty acids having an acyl chain of from about 8 to about 18 carbon atoms.

The ethoxylated alkylphenol nonionic surface active agents include various polyethylene oxide condensates of alkylphenols, especially the condensation products of monoalkylphenols or dialkylphenols wherein the alkyl group contains about 6 to about 12 carbon atoms in either branched chain or particularly straight chain configuration, for example, octyl cresol, octyl phenol or nonyl phenol, with ethylene oxide, said ethylene oxide being present in amounts equal to from about 5 to about 25 moles of ethylene oxide per mole of alkylphenol.

Ethoxylated aliphatic alcohol nonionic surface active agents include the condensation products of aliphatic alcohols having from about 8 to 18 carbon atoms in either straight chain or branched chain configuration, for example oleyl or cetyl alcohol, with ethylene oxide, said ethylene oxide being present in equal amounts from about 30 to about 60 moles of ethylene oxide per mole of alcohol.

Preferred nonionic surface active agents include: sorbitan esters (sold under the trade name Span) having the formula:

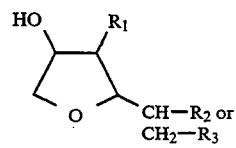

wherein
$R_1 = R_2 = OH$, $R_3 = R$ for sorbitan monoesters,
$R_1 = OH$, $R_2 = R_3 = R$ for sorbitan diesters,
$R_1 = R_2 = R_3 = R$ for sorbitan triesters,
where $R = (C_{11}H_{23})$ COO for laurate,
$(C_{17}H_{33})$ COO for oleate,
$(C_{15}H_{31})$ COO for palmitate,
$(C_{17}H_{35})$ COO for stearate.

Polyoxyethylene alkyl ethers (i.e. Brijs) having the formula:

$$CH_3(CH_2)_x(O-CH_2-CH_2)_yOH$$

where (x+1) is the number of carbon atoms in the alkyl chain, typically:

| lauryl | (dodecyl) |
|---|---|
| myristyl | (tetradecyl) |
| cetyl | (hexadecyl) |
| stearyl | (octadecyl) | and y is the number of ethylene oxide groups in the hydrophilic chain, typically 10–60.

Polyethylene sorbitan fatty acid esters, sold under the trade names of Polysorbates 20, 40, 60, 65, 80 & 85.

Polyethylene stearates, such as:
poly(oxy-1,2-ethanediyl), α-hydro- Ω-hydroxyoctadecanoate;
polyethylene glycol monostearate; and
poly(oxy-1,2-ethanediyl)-α-(1-oxooctadecyl)-Ω-hydroxypolyethylene glycol monostearate The film former polymeric materials used in accordance with the present invention include anionic polymers, cationic polymers and neutral polymers.

I Anionic Polymers

The anionic polymers carry negative charges in the ionized form and are capable of binding to cell surfaces mainly by electrostatic forces. Suitable anionic polymers include the following:

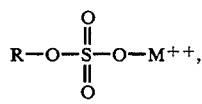

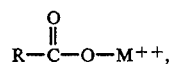

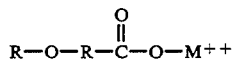

wherein
R is the polymeric chain;

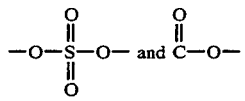

are anionic ligands; and $M^{++}$ is a divalent cation.

Specific anionic polymers useful in the practice of the present invention include:

Sulfated polysaccharides of the formula:

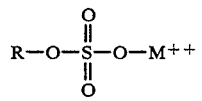

wherein
R is 3,6-anhydro-D-galactose linked through C-4 to D-galactose; (kappa carrageenan)
α-D-galactose units (1-3) linked; (lambda carrageenan)
D-galactose 3,6-anhydro-D-galactose; (iota carrageenan)
D-galactose 3,6-anhydro-L-galactose: (Agar-Agar)
D-galactose 3,6-anhydro-D-galactose; (Furcellaren)
D-glucopyranose; (Laminarin sulfate) Galactan; and (Galactan sulfate) Galactosamino-glucuronans (Chondroitin sulfates); and
$M^{++}$ is $Mg^{++}$, $Ca^{++}$, $Zn^{++}$, $Ba^{++}$ or mixtures thereof.

Carboxylated polysaccharides of the formula:

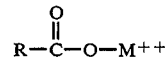

wherein R is D-galacturonoglycan; and (Pectin)
anhydro-D-mannuronic acid
and anhydro-L-guluronic acid (Algin)
residues; and $M^{++}$ is $Mg^{++}$, $Ca^{++}$, $Zn^{++}$, $Ba^{++}$ or mixtures thereof.

Cellulose derivatives of the formulae:

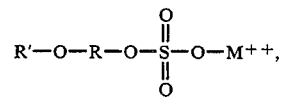

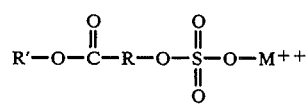

and

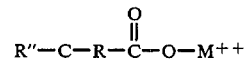

wherein
R is an anhydroglucose residue;
is $CH_3$, $C_2H_5$ or $C_3H_7$;
is $CH_3$ or $C_2H_5$; and
$M^{++}$ is $Mg^{++}$, $Ca^{++}$, $Zn^{++}$, $Ba^{++}$ or mixtures thereof.

Examples of cellulose derivatives include: sodium ethylcellulose sulfate, sodium cellulose acetate sulfate and sodium carboxymethyl cellulose.

Sulfated, sulfonated or carboxylated synthetic polymers of the formula:

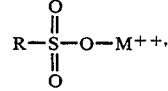

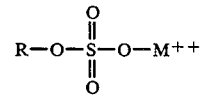

and

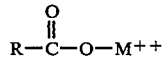

wherein
R is an aliphatic or aromatic hydrocarbon, such as polystyrene, poly(sulfon) resin or carboxylated (poly) vinyl; and
$M^{++}$ is $Mg^{++}$, $Ca^{++}$, $Zn^{++}$, $Ba^{++}$ or mixtures thereof.

II Cationic Polymers

The cationic polymers carry positive charges in the ionized form. Suitable polymers for practicing the present invention include: dermatan sulfate, keratosulfate, hyaluronic acid, heparin and chitin.

III Neutral Polymers

Neutral polymers having polarizable electrons such as oxygen, nitrogen, sulfur, fluoride, chloride, bromide and iodide are also suitable for practicing the present invention. In the presence of a cation, such as $Mg^{++}$, $Ca^{++}$, $Zn^{++}$ or $Ba^{++}$, the polymers are partially polarized thereby providing intermolecular interactions between the polymer and the intestinal wall. Examples of these polymers include:

- Polysaccharides, such as starch, glycogen, glucan, fructans, mannans, galactomannas, glucomannas, galactans, xylans, glycuranans, dextran and starch amylose;
- Cellulose derivatives, such as methylcellulose, hydroxyethylcellulose, ethylhydroxyethyl cellulose, hydroxypropyl methylcellulose and hydroxypropyl cellulose; and
- Synthetic polymers, such as polyvinylpyrrolidone, polyvinyl alcohol and ethylene oxide polymers.

The dosages of the contrast agent used according to the method of the present invention will vary according to the precise nature of the contrast agent used. Preferably, however, the dosage should be kept as low as is consistent with achieving contrast enhanced imaging. By employing as small amount of contrast agent as possible, toxicity potential is minimized. For most contrast agents of the present invention dosages will be in the range of from about 0.1 to about 16.0 g iodine/kg body weight, preferably in the range of from about 0.5 to about 6.0 g iodine/kg of body weight, and most preferably, in the range of from about 1.2 to about 2.0 g iodine/kg body weight for regular X-ray visualization of the GI tract. For CT scanning, the contrast agents of the present invention will be in the range of from about 1 to about 600 mg iodine/kg body weight, preferably in the range of from about 20 to about 200 mg iodine/kg body weight, and most preferably in the range of from about 40 to about 80 mg iodine/kg body weight.

The concentration of the contrast agent should be in the range of from about 0.001% w/v to about 75% w/v of the formulation, preferably from about 0.05% w/v to about 50% w/v and most preferably of from about 0.1% w/v to about 20% w/v.

The concentration of the film forming polymeric material depends on the particular polymer used, however, it should be in the range of 0.001 to about 15% w/v or higher in combination with a divalent substance, such as calcium lactate, having a concentration range of 0.001 to 15% w/v. Dosage level of the polymeric material may be in the range of from about 2 to about 15 g/kg body weight or higher.

The compositions of the present invention possess very good adherence to the walls of the gastrointestinal tract by forming an essentially uniform coating thereon.

The invention having been fully described, it will be apparent to one skilled in the art that changes and modifications can be made thereto without departing from the spirit and scope thereof.

What is claimed is:

1. An x-ray contrast composition designed for depositing a thin, flexible film membrane onto the mucosal lining of the nutrient absorbing inner surface of the intestine of a patient to form a barrier between said nutrient absorbing inner surface and the content of said intestine, said flexible film membrane to remain bound to said mucosal lining until eliminated by normal cell turnover comprising based on w/v:

(a) of from about 0.10 to about 15% of a polymeric material capable of forming a film membrane on the gastrointestinal tract in the pH range of from about 5 to about 8, said polymeric material is selected from the group consisting of anionic polymers carrying negative charges in the ionized form, cationic polymers carrying positive charges in the ionized form, and neutral polymers, said neutral polymers having polarizable electrons selected from the group consisting of oxygen, nitrogen, sulfur, fluoride, chloride, bromide and iodide; in combination with (b) of from about 0.10 to about 15% of a divalent cation to potentiate the binding of said flexible film membrane to said mucosal lining selected from the group consisting of $Ca^{++}$, $Mg^{++}$, $Zn^{++}$ and $Ba^{++}$; and (c) of from about 0.001 to about 75% of an x-ray contrast producing agent having the formula, or a pharmaceutically acceptable salt thereof

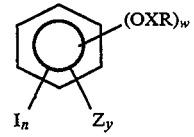

wherein

X is $-SO_2-$;

Z is H, halo, $C_1-C_{20}$alkyl, cycloalkyl, lower alkoxy, cyano, where the alkyl and cycloalkyl groups can be substituted with halogen or halo-lower-alkyl groups;

R is $C_1-C_{25}$ alkyl, cycloalkyl, or aryl each of which may be optionally substituted with halo, fluoro-lower-alkyl, lower-alkoxy, hydroxy, carboxy or lower-alkoxy carbonyl, lower-alkenyl, lower-alkynyl, lower-alkylene or lower-alkoxy-carbonyloxy, n is 1–5;

y is 0–4; and w is 1–4 in a pharmaceutically acceptable carrier.

2. The composition according to claim 1 wherein said x-ray contrast agent is selected from the group consisting of: 2,4,6-triiodoresorcinol, 2,4,6-triiodophenyl hexanesulfonate, 2,4,6-triiodophenyl heptanesulfonate, and 2,4,6-triiodophenyl decanesulfonate.

3. The x-ray contrast composition of claim 1 wherein said polymeric material is anionic having the formula:

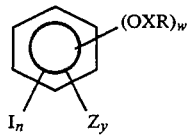

wherein
R is the polymeric chain;

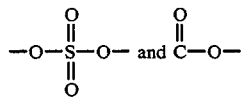

are anionic ligands; and
$M^{++}$ is a divalent cation.

4. The x-ray contrast composition of claim 3 wherein said anionic polymeric material is a sulfated polysaccharide having the formula:

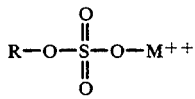

wherein
R is 3,6-anhydro-D-galactose linked through C-4 to D-galactose; (kappa carrageenan)
α-D-galactose units (1–3) linked; (lambda carrageenan)
D-galactose 3,6-anhydro-D-galactose; (iota carrageenan)
D-galactose 3,6-anhydro-L-galactose: (Agar-Agar)
D-galactose 3,6-anhydro-D-galactose; (Furcellaren)
D-glucopyranose; (Laminarin sulfate)
Galactan; and (Galactan sulfate)
Galactosamino-glucuronans (Chondroitin sulfates); and $M^{++}$ is $Mg^{++}$, $Ca^{++}$, $Zn^{++}$, $Ba^{++}$ or a mixture thereof.

5. The x-ray contrast composition of claim 3 wherein said anionic polymeric material is a carboxylated polysaccharide having the formula:

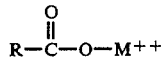

wherein
R is D-galacturonoglycan; and (Pectin) anhydro-D-mannuronic acid and anhydro-L-guluronic acid (Algin) residues; and
$M^{++}$ is $Mg^{++}$, $Ca^{++}$, $Zn^{++}$, $Ba^{++}$ or a mixture thereof.

6. The x-ray contrast composition of claim 3 wherein said anionic polymeric material is a cellulose derivative of the formula:

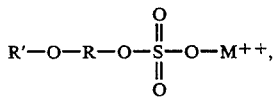

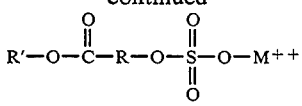

and

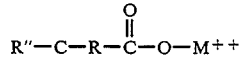

wherein
R is an anhydroglucose residue;
R' is $CH_3$, $C_2H_5$ or $C_3H_7$;
R'' is $CH_3$ or $C_2H_5$; and
$M^{++}$ is $Mg^{++}$, $Ca^{++}$, $Zn^{++}$, $Ba^{++}$ or a mixture thereof.

7. The x-ray contrast composition of claim 6 wherein said cellulose derivative is selected from the group consisting of sodium ethylcellulose sulfate, sodium cellulose acetate sulfate and sodium carboxymethyl cellulose.

8. The x-ray contrast composition of claim 1 wherein said anionic polymeric material is a sulfated, sulfonated or carboxylated synthetic polymer having the formula:

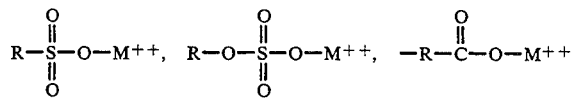

wherein
R is an aliphatic or aromatic hydrocarbon; and
$M^{++}$ is $Mg^{++}$, $Ca^{++}$, $Zn^{++}$, $Ba^{++}$ or a mixture thereof.

9. The x-ray contrast composition of claim 1 wherein said polymeric material is cationic selected from the group consisting of: dermatan sulfate, keratosulfate, hyaluronic acid, heparin and chitin.

10. The x-ray contrast composition of claim 1 wherein said polymeric material is a polysaccharide.

11. The x-ray contrast composition of claim 4 wherein said polysaccharide is selected from the group consisting of starch, glycogen, glucan, fructans, mannans, galactomannans, flucomannans, galactans, xylans, glycuranans, dextran and starch amylose.

12. The x-ray contrast composition of claim 1 wherein said polymeric material is a cellulose derivative.

13. The x-ray contrast composition of claim 6 wherein said cellulose derivative is selected from the group consisting of methylcellulose, hydroxyethyl cellulose, ethylhydroxyethyl and hydroxypropyl cellulose.

14. The x-ray contrast composition of claim 1 wherein said polymeric material is polyvinylpyrrolidone, polyvinyl alcohol or an ethylene oxide polymer.

15. The x-ray contrast composition of claim 1 wherein said pharmaceutical carrier contains at least one surfactant.

16. The x-ray contrast formulation of claim 9 wherein said surfactant is cationic.

17. The x-ray contrast formulation of claim 9 wherein said surfactant is anionic.

18. The x-ray contrast formulation of claim 9 wherein said surfactant is zwitterionic.

19. The x-ray contrast formulation of claim 15 wherein said surfactant is nonionic.

20. The x-ray contrast formulation of claim 16 wherein said cationic surfactant is selected from the group consisting of cetyl trimethyl ammonium bromide and dodecyl dimethyl ammonium bromide.

21. The x-ray contrast formulation of claim 17 wherein said anionic surfactant is selected from the group consisting of sodium lauryl sulfate, sodium heptadecyl sulphate, an alkyl benzene sulphonic acid, sodium butylnaphthalene sulfonate and sulphosuccinate.

22. The x-ray contrast formulation of claim 19 wherein said nonionic surfactant is selected from the group consisting of carboxylic esters, carboxylic amides, ethoxylated alkylphenols and ethoxylated aliphatic alcohols, sorbitan esters, polyoxyethylene alkyl ethers and polyoxyethylene sorbitan fatty acid esters.

23. A method of carrying out x-ray examination of the gastrointestinal tract of a patient, said method comprises the oral or rectal administration to the patient an x-ray contrast according to claim 1 and radiographing the gastrointestinal tract with a radiographic means.

24. The method of claim 23 wherein the amount of contrast agent administered to said patient is in the range of from about 0.1 to about 16.0 g iodine/kg body weight for regular x-ray visualization of the gastrointestinal tract.

25. The method of claim 23 wherein the amount of contrast agent administered to said patient will be in the range of from about 1 to about 600 mg iodine/kg body weight for CT scan visualization of the gastrointestinal tract.

* * * * *